United States Patent [19]

Zuk et al.

[11] Patent Number: 5,650,334
[45] Date of Patent: Jul. 22, 1997

[54] FLUORESCENT LABELLING COMPOSITIONS AND METHODS FOR THEIR USE

[75] Inventors: Robert F. Zuk, Burlingame; Sae Hyun Choo, Cupertino, both of Calif.

[73] Assignee: First Medical, Inc., Mountain View, Calif.

[21] Appl. No.: 521,860

[22] Filed: Aug. 31, 1995

[51] Int. Cl.$^6$ .................. G01N 33/544; G01N 33/53; G01N 33/58; G01N 33/60
[52] U.S. Cl. .................. 436/529; 436/508; 436/518; 436/519; 436/523; 436/524; 436/525; 436/528; 436/530; 436/800; 435/7.1; 435/7.92; 435/7.93; 435/7.94; 435/40.52; 435/174; 435/960; 435/968
[58] Field of Search .................. 435/7.1–7.21, 435/7.4, 7.5, 7.92, 7.93, 7.94, 40.52, 174, 960, 968; 436/508, 518, 519, 523, 524, 525, 529, 528, 530, 800

[56] References Cited

U.S. PATENT DOCUMENTS

| 3,864,089 | 2/1975 | Tiffany et al. | 23/258.5 |
|---|---|---|---|
| 3,873,217 | 3/1975 | Anderson et al. | 356/246 |
| 3,899,296 | 8/1975 | Mailen et al. | 23/259 |
| 3,901,658 | 8/1975 | Burtis et al. | 23/259 |
| 4,096,138 | 6/1978 | Scherr | 260/121 |
| 4,208,479 | 6/1980 | Zuk et al. | 435/7 |
| 4,225,558 | 9/1980 | Peterson et al. | 422/72 |
| 4,279,862 | 7/1981 | Bretaudiere et al. | 422/72 |
| 4,284,602 | 8/1981 | Kelton et al. | 422/72 |
| 4,314,968 | 2/1982 | Guigan | 422/64 |

(List continued on next page.)

FOREIGN PATENT DOCUMENTS

| 0 288 179 | 10/1988 | European Pat. Off. | G01N 33/577 |
|---|---|---|---|
| 0 467 782 | 1/1992 | European Pat. Off. | G01N 33/573 |
| 80/02076 | 10/1980 | WIPO . | |

OTHER PUBLICATIONS

Gosling, J. A Decade of Development in Immunoassay Methodology, Clin. Chem. 36/8, 1408–1427. 1990.

Hurni et al., Detection of Antibody to the PRES2 Sequence of the Hepatitis B Virus Envelope Protein Using an Immuno–Ligand Assay with a Silicon Sensor Detection System, Jour. of Immuno. Method., 145, 19–26. 1991.

Ullman et al., Homogeneous Fluorescence Immunoassays, Clinical Laboratory Techniques for the 1980s, 13–43. 1980.

Zuk et al., Fluorescence Protection Immunoassay: A New Homogeneous Assy Technique, Clin. Chem. 25/9, 1554–1560. 1979.

"FluoroLink™ Cy5™ Reactive Dye 5–Pack, Cat. No. A2400," (1995) Biological Detection Systems, Inc., Product Brochure.

deBelder, A. N. et al. "Preparation and properties of fluorescein–labelled dextrans," (1973) *Carbohydrate Research*, 30:375–378.

Glabe, C. G. et al. "Preparation and Porperties of Fluorescent Polysaccharides," (1983) *Analytical Biochemistry* 130:287–294.

Southwick, P. L. et al. "Cyanine dye labeling Reagents–Carboxymethylindocyanine Succinimidyl Esters[1]," (1990) *Cytometry* 11:418–430.

Mujumdar, R. B. et al. "Cyanine Dye Labeling REagents: Sulfoindocyanine Succinimidyl Esters," (1993) *Bioconjugate Chem.* 4:105–111.

*Primary Examiner*—James C. Housel
*Assistant Examiner*—Bao-Thuy L. Nguyen
*Attorney, Agent, or Firm*—Townsend and Townsend and Crew LLP

[57] ABSTRACT

A fluorescent labelling composition comprises a linear polysaccharide backbone molecule having a plurality of target-binding molecules, such as antibodies or nucleic acids, attached at spaced-apart intervals thereon. Each of the target-binding molecules, in turn, includes a multiplicity of fluorescent dye molecules bound thereto. In this way, fluorescent signal introduced to a single target-site on a solid phase surface may be increased without loss of binding activity.

12 Claims, 2 Drawing Sheets

U.S. PATENT DOCUMENTS

| | | | |
|---|---|---|---|
| 4,353,982 | 10/1982 | Gomez et al. | 435/7 |
| 4,624,961 | 11/1986 | Welstead, Jr. | 514/403 |
| 4,690,907 | 9/1987 | Hibino et al. | 436/514 |
| 4,740,472 | 4/1988 | Burtis et al. | 436/63 |
| 4,788,154 | 11/1988 | Guigan | 436/180 |
| 4,810,639 | 3/1989 | Pankratz | 435/7 |
| 4,876,203 | 10/1989 | Guigan | 436/45 |
| 4,894,204 | 1/1990 | Cornut | 422/72 |
| 4,900,662 | 2/1990 | Shah et al. | 435/7 |
| 4,912,033 | 3/1990 | Ladenson et al. | 435/7 |
| 4,970,144 | 11/1990 | Fareed et al. | 435/5 |
| 5,009,996 | 4/1991 | Shah et al. | 435/7 |
| 5,009,997 | 4/1991 | Shah et al. | 435/7.4 |
| 5,011,771 | 4/1991 | Bellett et al. | 435/7.94 |
| 5,186,844 | 2/1993 | Burd et al. | 210/782 |
| 5,188,939 | 2/1993 | Mangold et al. | 435/7.92 |
| 5,202,234 | 4/1993 | Shah et al. | 435/7.4 |
| 5,242,606 | 9/1993 | Braynin et al. | 210/787 |
| 5,258,041 | 11/1993 | Guire et al. | 623/66 |
| 5,268,486 | 12/1993 | Waggoner et al. | 548/427 |
| 5,316,784 | 5/1994 | Maurer et al. | 427/2 |
| 5,332,395 | 7/1994 | Gero | 435/71 |
| 5,382,515 | 1/1995 | Shah et al. | 435/7.4 |
| 5,382,522 | 1/1995 | Shah et al. | 435/7.4 |
| 5,468,649 | 11/1995 | Shah et al. | 436/518 |
| 5,468,651 | 11/1995 | Self | 436/548 |
| 5,486,479 | 1/1996 | Ito et al. | 436/533 |
| 5,486,616 | 1/1996 | Waggoner et al. | 548/217 |

FLUORESCENT LABELLING COMPOSITIONS AND METHODS FOR THEIR USE

BACKGROUND OF THE INVENTION

The subject matter of the present application is related to that disclosed in each of the following U.S. patent applications which are being filed on the same day: U.S. Ser. Nos. 08/522,048; 08/522,434; 08/521,615; 08/522,435, the full disclosures of which are incorporated herein by reference.

1. Field of the Invention

The present invention relates generally to compositions and methods for detecting target substances in biological samples. More particularly, the present invention relates to labelling compositions comprising a multiplicity of fluorescent dye molecules bound to a plurality of binding molecules which in turn are bound to a linear polysaccharide backbone.

Many methods are known for detecting specific biological substances in solution and on solid phase supports. Of particular interest to the present invention are immunochemical methods where binding of a detectable label to a target substance in a biological sample is mediated by a specific binding substance. For example, a labelled specific binding substance, such as a fluorescently-labelled antibody, which recognizes the target substance (e.g., an antigen or hapten) is exposed to a biological specimen suspected of containing the target substance, and presence of the target substance is confirmed by binding of the label. Similar techniques may be performed using nucleic acid hybridization methods, where nucleic acid sequences of interest may be detected with a labelled polynucleotide which recognizes its complementary sequence in the nucleic acids of the biological specimen. In both cases, if present, the target substance will thus bind to the fluorescent label, allowing detection based on fluorescent emissions of the label.

Fluorescent labels offer a number of advantages compared with other common assay labels, such as enzyme labels. The detection of fluorescent labels is simple and does not require the addition of a substrate as is common with many enzyme labels. The signal generated by fluorescent label is localized, permitting the detection of multiple analytes in different reaction zones within a single reaction region or chamber. Thus, fluorescent labels allow simplified protocols for the detection of multiple analytes where only the final detection step must be performed separately for different analytes.

Of specific interest to the present invention, a class of cyanine fluorescent materials, referred to as "arylsulfonate cyanine fluorescent dyes," having particularly desirable properties has been developed. The arylsulfonate cyanine fluorescent dyes have high extinction coefficients (typically from 130,000 L/mole to 250,000 L/mole, good quantum yields, fluorescent emission spectra in a range (500 nm to 750 nm) which is outside of the autofluorescence wavelengths of most biological materials and plastics, good solubilities, and low non-specific binding characteristics. A particular arysulfonate cyanine fluorescent dye, designated Cy5, has the following structure:

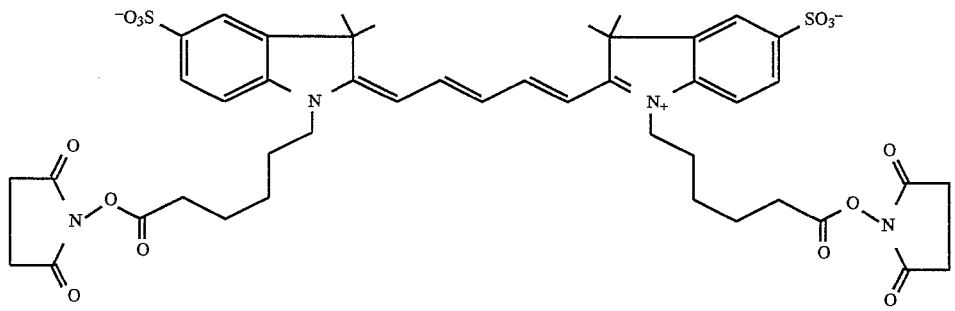

Despite these excellent properties, arylsulfonate cyanine fluorescent dyes suffer from certain limitations. In particular, these dyes have a relatively narrow Stokes shift which results in significant overlap between the excitation and emission spectra of the dye. The overlap of excitation and emission spectra, in turn, can cause self-quenching of the fluorescence when the dye molecules are located close to each other when excited. Such self-quenching limits the number of arylsulfonate dye molecules which can be conjugated to a single antibody molecule for use in immunoassays. In the case of Cy5, an exemplary arylsulfonate cyanine fluorescent dye, the Stokes shift is 17 nm (which is the difference between an excitation wavelength of 650 nm and an emission wavelength of 667 nm). Optimal fluorescent yield is obtained when from two to four Cy5 molecules are conjugated to a single antibody molecule. The fluorescent signal output drops rapidly when more than four dye molecules are conjugated to a single antibody molecule. The inability to conjugate more than four dye molecules to individual antibody molecules significantly limits the sensitivity of immunoassays using Cy5-labelled antibodies and other binding substances.

The direct attachment of fluorescent dye molecules to carrier molecules, such as dextran, has been proposed as the technique for enhancing fluorescent output. Such carrier molecules would typically contain one or a few antibody molecules, where the binding of each antibody to a target substance will carry a number of fluorescent dye molecules. Attachment of arylsulfonate cyanine dyes to such carrier molecules, however, would not be expected to significantly increase the level of fluorescent emission because of the self-quenching density of the individual dye molecules, as described above. Moreover, the binding capacity of many prior fluorescent dyes/carrier molecules complexes has been limited, due both to a limited number of antibody molecules present in the complex and to steric hinderance of the antibodies from the carrier molecule.

For these reasons, it would be desirable to provide improved fluoresceht labelling compositions for use in the detection of target substances in biological samples. Such compositions should be useful in all circumstances where fluorescent labelling complexes generally find use, including solid phase immunoassays, immunohistochemical staining, flow cytometry, and the like. It would be particularly desirable to provide improved arylsulfonate cyanine dye compositions comprising conjugates having multiple dye molecules with reduced self-quenching and relatively high target-binding capacities. Such compositions should continue to display the low non-specific binding, high solubility, and other desirable characteristics associated with previous arylsulfonate cyanine dye formulations.

2. Description of the Background Art

Arylsulfonate cyanine fluorescent dyes are described in Mujumdar et al. (1993) *BIOCONJUGATE CHEMISTRY* 4:105–111; Southwick et al. (1990) *CYTOMETRY* 11:418–430; and U.S. Pat. No. 5,268,486. Cy5 is described in each of the references and is commercially available from Biological Detection Systems, Inc., Pittsburgh, Pa., under the tradename Fluorolink™ Cy5™. Fluorescently labelled polysaccharides, such as dextrans, are described in Globe et al. (1983) *ANAL. BIOCHEM.* 130:287 and deBelder et al. (1973) *CARBOHYDRATE RES.* 30:376.

SUMMARY OF THE INVENTION

The present invention provides compositions and methods for highly sensitive fluorescent detection of target substances and biological samples. The compositions are fluorescent labelling compositions comprising a carrier or backbone molecule having a plurality of target-binding molecules bound thereto. Each target-binding molecule, in turn, has a multiplicity of fluorescent dye molecules bound thereto. The backbone molecule is a linear polysaccharide, such as a high molecular weight dextran, and the target-binding molecules are antibodies, nucleic acids, or the like, bound at spaced-apart locations along the linear polysaccharide. Such compositions are particularly suitable for incorporating arylsulfonate cyanine fluorescent dyes, such as Cy5, where they provide substantially enhanced fluorescent emission levels (signal amplification) with reduced self-quenching.

The compositions of the present invention may be advantageously employed in virtually any assay or labelling procedure where fluorescent label is to be introduced to a target substance via specific binding, including solid phase and other heterogenous immunoassays, immunohistochemical staining of biological specimens, flow cytometry, and the like. The compositions will be particularly useful in performance of solid phase assays where the labelling composition is exposed to a solid phase surface having the target substance bound directly or indirectly thereto. An especially preferred use is in two-site or "sandwich" solid phase assays where the solid phase surface is derivatized with a binding substance specific for a target substance suspected of being present in a liquid sample. After exposure to the liquid sample, the solid phase is washed and exposed to the labelling composition of the present invention which binds directly or indirectly (e.g., through the intermediate binding of biotin and avidin/streptavidin) to the immobilized target substance. The fluorescent label is then detected on the solid phase surface by exposure to excitation energy within a localized reaction zone on the surface.

DESCRIPTION OF THE PREFERRED EMBODIMENT

Figure 1:
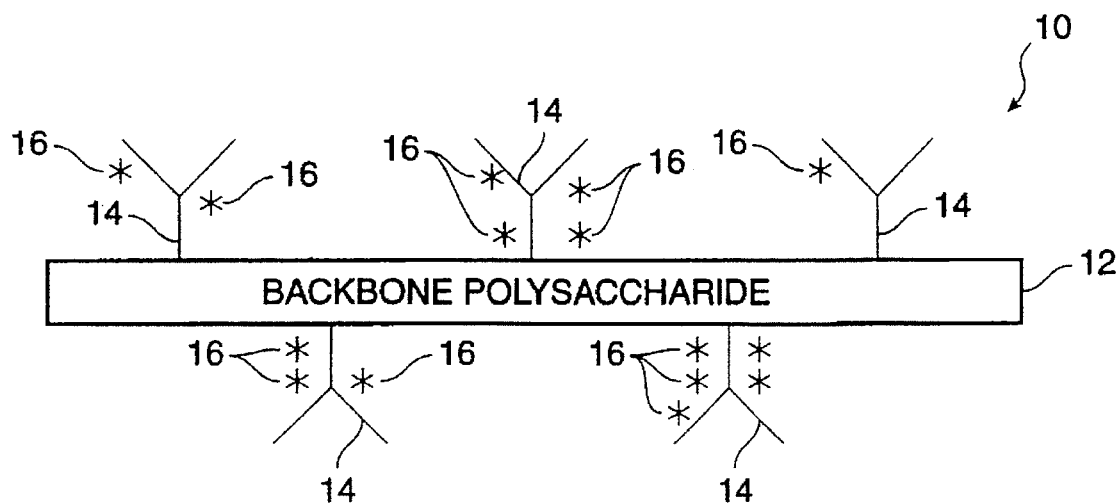
FIG. 1 is a schematic illustration showing the structural relationship of the polysaccharide backbone, the target-binding substance, and the fluorescent label in the fluorescent labelling compositions of the present invention.

Fluorescent labelling compositions according to the present invention comprise conjugates 10 (FIG. 1) including a backbone or carrier molecule 12, a plurality of target-binding molecules 14, and a multiplicity of fluorescent dye molecules 16 attached to each of the target-binding molecules. The backbone or carrier molecule 12 will comprise a linear polysaccharide, usually consisting of a single linear polysaccharide molecule. Conjugate 10 will include at least two target-binding substances 14, usually including at least four target-binding substances, and preferably including from five to 20 target-binding substances, more preferably from six to 15 target-binding substances. Each of the target-binding substances 14 will preferably include at least one fluorescent dye molecule, more preferably including at least two fluorescent dye molecules, and often including three or more fluorescent dye molecules. For many fluorescent dyes, the upper limit on the number of dye molecules will be 5, 10, or even higher. In the exemplary case of arylsulfonate cyanine fluorescent dyes, however, the optimum number of fluorescent dye molecules will be from 2 to 4 dye molecules per antibody binding substance 14.

The compositions and methods of the present invention may be used for labelling and detecting a wide variety of target substances in various biological samples. The term "target substance" is used herein as defined as a molecule, compound, or other composition which is suspected of being present in a biological sample or on a solid phase surface, as described hereinafter. The target substance will be detectable through binding through a target-binding substance as described below, and will usually be a biological molecule, such as a polypeptide, protein, carbohydrate, or nucleic acid, and may thus be associated with a particular biological, pharmacological, genetic, or biochemical property or set of properties. A non-exhaustive list of exemplary analytes is set forth in U.S. Pat. No. 4,366,241, at col. 19, line 7 through col. 26, line 42, the disclosure of which is incorporated herein by reference.

Target substance may be present in or separated from a variety of biological specimens, such as blood, serum, plasma, urine, cerebral fluid, spinal fluid, ocular lens liquid (tears), saliva, sputum, semen, cervical mucus, scrapings, swab samples, and the like, of the type frequently employed in the diagnosis in monitoring of diseases and therapeutic treatments. In addition to such medical samples, the compositions and methods of the present invention may be used to detect target substances in industrial, environmental, and food samples, such as water, process streams, milk, meat, poultry, fish, condition media, and the like. In certain circumstances, it may be desirable to pretreat the sample, such as by liquification, separation, solubilization, concentration, filtration, chemical treatment, or a combination of such treatment steps, in order to improve the compatibility of the sample with the remaining steps of the assay, as described hereinafter. In particular, it will frequently be desirable to pretreat a sample in order to permit reaction with a solid phase surface in order to capture a target substance on the surface prior to detection with the fluorescent compositions and methods of the present invention. The selection and pretreatment of biological, industrial, and environmental samples prior to immunological testing is well know in the art and need not be described further.

The term "target-binding substance" as used herein will refer to any macromolecular compound having spatial and polar features which cause it to bind specifically to another compound or feature in a complex biological material. Such target-binding substances useful in the present invention will be selected or prepared to specifically bind to particular target compositions, such as the target substances defined above. Natural specific binding pairs which may provide the target-binding substances include antibodies and antigens, lectins and carbohydrates, hormones and hormone receptors, enzymes and enzyme substrates, biotin and avidin/strep avidin, vitamins and vitamin-binding proteins, complementary polynucleotide sequences, drugs and receptors, enzymes and reaction products, enzymes and enzyme inhibitors, apoproteins and cofactors, immunoglobulins and receptors, organisms and receptors, growth factors and receptors, chelating agents and metals, and the like. Biotin and avidin, including biotin derivatives and avidin derivatives such as streptavidin, may also be used as intermediate binding substances in assay protocols employing complex binding sequences. For example, antibodies may be labelled with biotin ("biotinylated") and used to bind to a target substance previously immobilized on a solid phase surface. Fluorescent compositions according to the present invention employing an avidin target-binding substance may then be used to introduce the fluorescent label. When no natural specific binding substances exist (as will usually be the case), a specific target-binding substance may be prepared. For antigenic and haptenic target substances, antibodies may be prepared by well-known techniques. For polynucleotides, complementary polynucleotides, including both DNA and RNA molecules, may be prepared by well known synthesis techniques.

Suitable backbone or carrier molecules for incorporation into the labelling conjugates of the present invention will be linear polysaccharides having molecular weights above 500 kD, preferably above 750 kD, and more preferably above 1000 kD. Exemplary linear polysaccharides include dextran, FICOLL®, and the like. Particularly preferred is the use of dextran molecules having molecular weights above 100 kD, preferably above 1500 kD, and frequently 2000 kD or higher. A preferred linear polymer is dextran having a molecular weight of 2000 kD.

The compositions of the present invention may incorporate virtually any fluorescent label which may be covalently or non-covalently (preferably covalently) attached to the binding substance. In the case of both protein and nucleic acid target-binding substances, suitable fluorescent labels include fluorescent dyes, fluorescein, Texas Red, and the like. In both cases, the preferred fluorescent label will be an arylsulfonate cyanine fluorescent dye, such as those described in U.S. Pat. No. 5,268,486, the full disclosure of which is incorporated by reference. Particularly preferred is the arylsulfonate cyanine fluorescent dye designated Cy5, in that patent.

Attachment of the fluorescent label to the target-binding substance may be covalent or non-covalent, preferably being covalent. The manner of covalent attachment will depend on the precise nature of both the label and the target-binding substance. When the target-binding substance is a polypeptide or protein, such as an antibody, the fluorescent label may be covalently bound to it through a variety of moieties, including disulfide, hydroxyphenyl, amino, carboxyl, indole, or other functional groups, using conventional conjugation chemistry as described in the scientific and patent literature. Alternatively, antibodies may be biotinylated by known techniques (see Wilchek and Bayer, (1988) *ANAL. BIOCHEM.* 171:1–32) and linked to the fluorescent label via avidin molecules (where the fluorescent label-avidin conjugate may comprise the fluorescent labelling composition of the present invention).

Covalent binding of the fluorescent label to a polynucleotide target-binding substance may be effected through a variety of moieties, including aldehyde, ketone, isothiocyanate, imidate, inosine, acyl, and alkyl, using conventional conjugation chemistry, while derivatization with biotin is taught in numerous references. (See Leary et al. (1983) *PROC. NATL. ACAD. SCI. USA* 80:4045–4049; WO86/02929; EP063 879; Langer et al. (1981) *PROC. NATL. ACAD. SCI. USA* 78:6633–6637; and EP2009 996). Numerous other references are available which teach methods for binding fluorescent labels to nucleic acid molecules.

Exemplary techniques for binding arylsulfonate cyanine fluorescent dye labels to antibodies and other proteins are described in U.S. Pat. No. 5,268,486, the full disclosure of which has previously been incorporated by reference. Techniques for linking the preferred Cy5 fluorescent label to both antibodies and nucleic acids are described in a technical bulletin identified as Cat. No. A25000, published by Biological Detection Systems, Inc., Pittsburgh, Pa.

The target-binding substances will be bound to the linear polysaccharides using known procedures for linking proteins and/nucleic acids to carbohydrates. For example, Manube et al. (1983) *BIOCHEM. BIOPHYS. RES. COMM.* 115:1009, describes conjugation of the anti-cancer agent, mitomycin, to a monoclonal antibody conjugated to dextran. The dextran enhanced the cytotoxic effect of the drug by crosslinking the antibody. Scheffler et al. (1972) *J. BIOL. CHEM.* 247:18, developed a method to link polynucleic acids to FICOLLi® and dextran to study the activity of DNA polymerases. McMaster et al. (1975) *CELL. IMMUNOLOGY* 20:42–53, prepared dinitrophenolficoll to monitor hapten specific B cell immune response. There are a variety of chemical approaches to effect linkage of the target binding substance to the linear polysaccharides. Crosslinking reagents directed towards carboxyl, sulfhydryl, and amino groups can be employed. Wong gives a comprehensive description in "Chemistry of Protein Conjugation and Crosslinking," CRC Press. The number of antibodies bound per polysaccharide molecule will depend on the molar ratio of antibody to polysaccharide (dextran) during the conjugation reaction.

The labelling compositions of the present invention will be prepared from the molecular components described above using the conjugation chemistries also described above. After preparation, the compositions will be separated and purified using conventional separation techniques, such as gel filtration, HPLC, and the like. Typically, the compositions of the present invention will be at least 90% pure by weight, preferably being at least 95% pure by weight, and usually being 99% pure by weight, or higher.

The fluorescent labelling compositions of the present invention will frequently be employed to detect target substances present on solid phase surfaces. As used herein, the term "solid phase surface" will include any biological or non-biological surface capable of supporting or capturing the target substance. When used in heterogenous immunoassays, the solid phase surface will typically be a plastic (e.g., acrylic), glass, membrane, or other non-biological surface having a target-binding substance previously immobilized thereon. Specific methods for immobilizing capture antibody of other binding substances are described in copending application Ser. Nos. 08/374,265 and 08/522,435 the full disclosures of which are incorporated herein by reference.

The solid phase may then be used to react with a biological sample to capture target substance which may be present therein. Such solid phase surfaces are frequently used in two-site immunometric assays which utilize two antibodies, each of which is present in excess over the amount of target substance in the sample. The relatively high concentrations of target-binding substance and of labeled target-binding substance assures that all target substance is captured and detected. A particular protocol for performing such two-site immunometric assays will be described below in connection with FIGS. 2A and 2B.

The fluorescent labelling compositions of the present invention will also be useful with biological solid phase surfaces, including tissue sections, intact cells, biological membranes, organslies, chromosomes, and the like. The compositions will also be useful with non-biological membranes which are prepared by the transfer of a desired target substance from a primary biological material, e.g., by blotting.

Figure 2A:
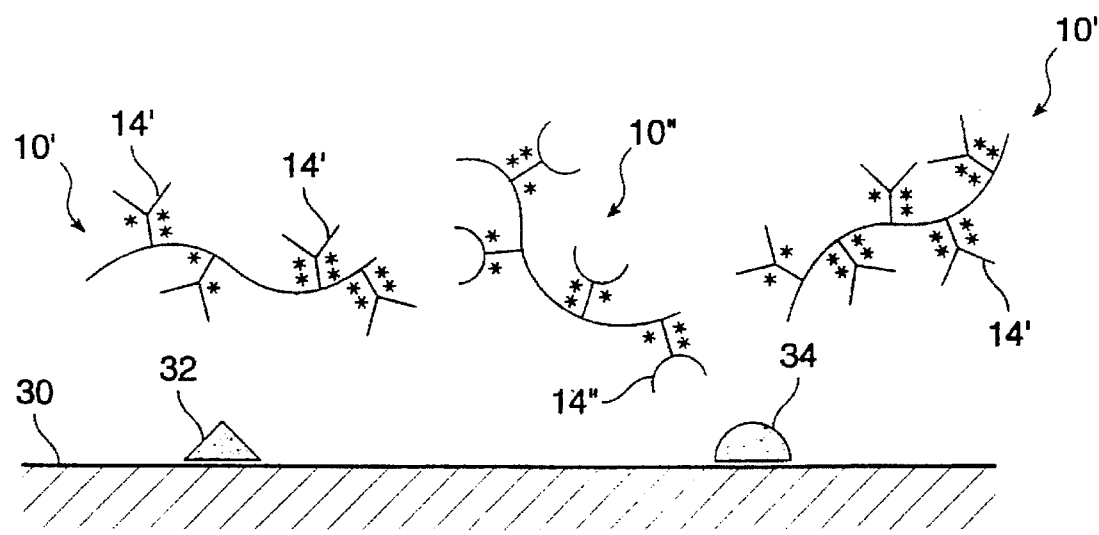
FIGS. 2A and 2B illustrate a method according to the present invention using the fluorescent labelling composition of FIG. 1 for detecting target substances in two discrete reaction zones on a solid phase surface.
Figure 2B:
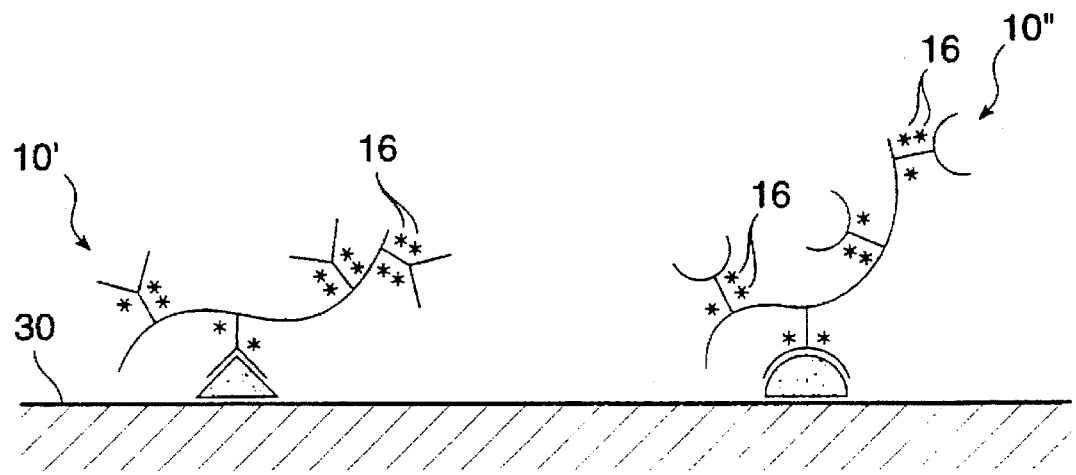

Referring now to FIGS. 2A and 2B, an exemplary two-site immunometric assay performed using the fluorescent labelling compositions of the present invention will be described. A solid phase surface 30 includes a first target substance 32 and an immunologically distinct second target substance 34. The target substances 32 and 34 may be any of the types of substances described above, including proteins, carbohydrates, nucleic acids, and the like. At least two types of fluorescent labelling conjugates 10' and 10" are exposed to the solid phase surface 30, typically in an aqueous solution which permits which permits conjugates to migrate until they recognize their specific target substance. Conjugate 10' includes target-binding substances 14 which are specific for the target substance 32, while conjugate 10" includes target-binding substances 14" which are specific for the target substance 34. After sufficient incubation time, typically from 60 seconds to 600 seconds, the conjugates 10' and 10" will bind to their respective target substances 32 and 34, respectively, as illustrated in FIG. 2B. After washing to remove non-bound labelling conjugate, the discrete reaction zones on the solid phase surface 30 may be separately interrogated with excitation energy having a wavelength selected to excite the particular fluorescent label 16 which is employed. While the same fluorescent label 16 will usually be employed in both conjugates 10' and 10", the physical isolation of the reaction zones in which the conjugates are bound permits separate detection without interference. Thus, the amounts of both target substance 32 and 34 may be independently measured on a single solid phase surface.

Figure 3:
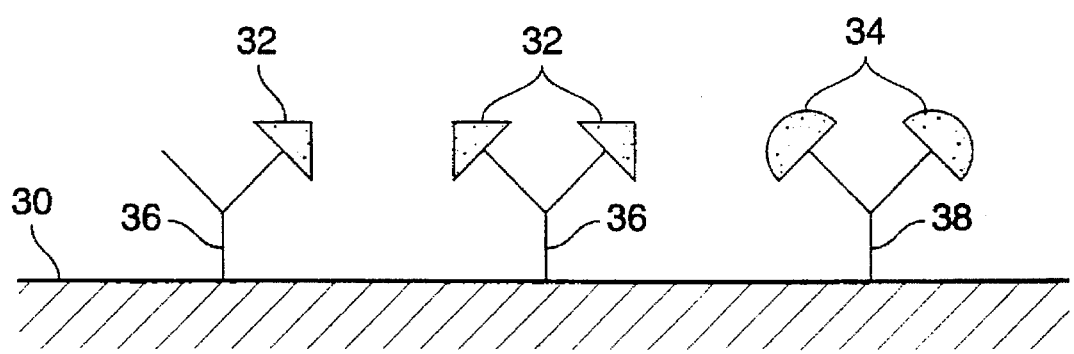
FIG. 3 illustrates the use of specific binding substances for capturing a target substance onto a solid phase according to the method of the present invention.

It will be appreciated that target substances 32 and 34 will typically be introduced to the solid phase surface 30 using specific binding substances, such as capture antibodies 36 and 38, respectively (FIG. 3), which have previously been immobilized on the surface. Such aspects of two-site immunometric assays are well known in the art The following examples are offered by way of illustration not by way of limitation.

EXPERIMENTAL

Materials and Methods

1. Preparation of Cy5-Antibody-Dextran Conjugates

To thiolate dextran, 150 µl of a 34 mg/ml solution of succinimydyl 6-[3-[2-pyridyldithio]-proprionamido] hexanoate (LC-SPDP) (Pierce #21651) in dimethylformamide (DMF) was added to a 5 ml solution containing 20 mg/ml aminodextran (Molecular Probes, #D-7145, 130 amines/dextran, 2000 kD M.W.) in phosphate buffered saline (PBS) pH 7.4. The reaction proceeded for 30 minutes at room temperature (RT), then the mixture was dialyzed overnight at RT against PBS. Greater than 95% of the amines in aminodextran were labeled with LC-SPDP during the reaction. The LC-SPDP-dextran was then purified on a Bio Gel® A5m column (1×100 cm). To remove the low molecular weight dextran fragments, only the fractions of the first peak were collected.

A 6.15 ml solution of anti-CKMM antibody (BiosPacific G31520) at 2.6 mg/ml in PBS pH 7.4 was mixed with 156 µl of 2.7 mg/ml succinimidyl 4-[N-malemidomethyl] cyclohexan-1-carboxylate (SMCC) (Pierce #22320) in DMF and was allowed to react for 30 minutes at RT. Unreacted SMCC was removed by purification on a Sephadex$^e$ G25 column.

The LC-SPDP-dextran was reduced by adding 156 µl of 0.5M dithiothreitol to 5.2 ml of 3.1 mg/ml LC-SPDP-dextran and incubating for 15 minutes at 2 RT. The dextran was then purified on a PD-10 (Pharmacia #17-0851-01) column in PBS pH 7.4.

Conjugation was achieved by mixing the reduced LC-SPDP-dextran with the SMCC-anti-CKMM and incubating overnight at RT. n-ethyl-maleimide (NEM) (Sigma #12828-7) was added at a final concentration of 1.0 mM to stop the reaction. The conjugate was then concentrated down to 6 ml in a Centricon Concentrator (Amicon #4211), and the buffer was exchanged to 0.1M sodium carbonate pH 9.3.

The anti-CKMM/dextran was labeled with Cy5 at a molar coupling ratio (antibody:dye) of 1:4 by adding 0.1 mg of Cy5 (Biological Detection Systems 1464C-1) to 1.3 ml of the concentrated conjugate. After 30 minutes at RT, the conjugate was purified on a PD-10 column to remove free Cy5, and then purified on a Bio Gel® A5m column (1×100 cm) to remove unconjugated antibody. Spectral analysis of the conjugate indicated 2.9 Cy5 molecules per antibody. Approximately 10 antibodies were linked to dextran assuming an average molecular weight of 2000 kD.

2. CKMB Assay Materials

Reaction wells having benzophenone bovine serum albumin (BSA)-biotin immobilized on the bottom were prepared as follows. Each reaction well was assembled by attaching a teflon ring on the surface of an acrylic disk obtained from the Germanow-Simon company, using double stick tape 415 from the 3M company. The dimensions of teflon ring were 9 mm inner diameter and 1.5 mm height. The dimensions of acrylic disk were 30×30 mm sides and 0.6 mm thick, on which four teflon rings were attached. The teflon rings were etched with $CO_2$ to improve bonding of the rings onto the disk. Benzophenone BSA-biotin was then immobilized at 40 µg/ml by UV-curing for 10 minutes.

Streptavidin-monoclonal anti-CKMB antibody conjugate (SA-anti-CKMB) was prepared using heterobifunctional linking reagents, S-acetylthioglycolic acid N-hydroxysuccinimide ester (SATA, Pierce #26102), and Succinimidyl 4-(N-maleimidomethyl) cyclohexane-1-carboxylate (SMCC, Pierce #22320). Fifteen (15) molar excess of SATA (dissolved at 5 mg/mL in dimethylformamide (DMF) from Pierce) was reacted with 1 mg of anti-CKMB at 0.74 mg/mL in PBS at pH 7.4 for 3 hours at room temperature. Also, 15 molar excess of SMCC (dissolved at 5 mg/mL in DMF) was reacted with 1.1 mg of streptavidin at 1.1 mg/mL in PBS for 3 hours at room temperature. Unreacted linkers were removed from both antiCKMB/SATA and streptavidin/SMCC reaction mixtures using Sephadex® G25M column (PD10 column from Pharmacia).

The purified antiCKMB-SATA and streptavidin-SMCC were mixed at the protein molar ratio of 1:3. The conjugation reaction was initiated by adding 1M hydroxylamine to a final concentration of 100 mM and incubated over 18 hours at 4° C. The reaction was stopped by adding 100 mMN-ethylmaleimide (NEM) from Aldrich Chemical at a final concentration of 1 mM in the reaction mixture and incubating for 15 minutes at room temperature. After the incubation with NEM, the conjugation reaction mixture was concentrated to a final volume less than 2 mL using a Centricon-100 concentrator from Amicon. Then the concentrated mixture was purified using a Bio-Gel® A-5m column (1×100 cm) from Bio-Rad to isolate streptavidin-antiCKMB conjugate.

Cy5/anti-CKMM-Dx conjugate was prepared as described above.

SA-anti-CKMB dilution buffer was 0.1% BSA and 0.05% Tween® 20 in PBS, pH 7.4. Assay Buffer was 4% HSA, 150 µg/ml mouse IgG, and 0.05% Tween® 20 in PBS, pH 7.4. Wash Buffer was 0.2% Tween® 20 in PBS, pH 7.4.

3. CKMB Assay Protocol

SA-anti-CKMB solution (7.5 µg/ml) was added to SA-anti-CKMB dilution buffer. 50 µL of this solution was added into reaction wells and incubated for 1 hour at 37° C. Wells were washed by immersing the entire disk into wash buffer. The wash step was repeated 5 times in five different containers containing wash buffer. Excess wash buffer was removed from the wells using a micropipet. Samples (50 µl) containing CKMB was added into the reaction wells and incubated for 10 minutes at room temperature. Wells were washed by immersing the entire disk into wash buffer. The wash step was repeated 5 times in five different containers containing wash buffer. Excess wash buffer was removed from the wells using a micropipet. Cy5/anti-CKMM-Dx conjugate (50 µl) was added at the proper loading and incubated for 5 minutes at room temperature. Wells were washed by immersing the entire disk into wash buffer. The wash step was repeated 5 times in five different containers containing wash buffer. Excess wash buffer was removed from the wells using a micropipet. Wash buffer (50 µl) was added into each well, and the Cy5 signal read using a reader.

RESULTS

The results are shown in Tables 1 and 2, below. The results of Table 1 are from a CKMB assay run with 0 (control) and 100 ng/ml samples and Cy5-labelled anti-CKMM. Assays employing Cy5-anti-CKMM-dextran can have up to a six-fold higher fluorescent signal with positive CKMB samples.

The fluorescent signal with negative samples (resulting from non-specific binding of the Cy5-antibody, was not increased when compared with the dextran conjugate and native antibody. Consequently, the signal-to-background ratio is improved with dextran conjugates.

Table 2 illustrates data from CKMB assays employing Cy5-anbtibody-dextran conjugates with dextrans of varying molecular weight. Dextran (200 kD) maximizes the available signal.

TABLE 1

Monomeric Anti-CKMM-Cy5 vs. Polymeric Cy5-Anti-CKMM/Dextran Conjugates

| Conjugates | Loading (µg/ml) | [CKMB] (ng/ml) | Fluorescence (mV) Mean | SD |
|---|---|---|---|---|
| Anti-CKMM-Cy5 | 10 | 0 | 3.00 | 0.19 |
| | | 100 | 19.13 | 0.86 |
| | 40 | 0 | 3.98 | 0.41 |
| | | 100 | 20.47 | 1.54 |
| | 80 | 0 | 5.03 | 1.11 |
| | | 100 | 20.94 | 1.85 |
| Anti-CKMM-Cy5/Dextran (2000KD) | 10 | 0 | 2.96 | 0.50 |
| | | 100 | 59.67 | 1.06 |
| | 40 | 0 | 2.45 | 0.11 |
| | | 100 | 82.90 | 5.90 |
| | 80 | 0 | 2.98 | 0.09 |
| | | 100 | 124.83 | 5.89 |

TABLE 2

Comparison of Cy5-Anti-CKMM/Dextran Conjugates in Various Sizes

| Cy5-Anti-CKMM/Dextran Dextran Molecular Wt. | Loading (µg/ml) | [CKMB] (ng/ml) | Fluorescence (mV) Mean | SD |
|---|---|---|---|---|
| 70 KD | 40 | 0 | 1.72 | 0.23 |
| | | 100 | 28.85 | 4.77 |
| | 80 | 0 | 2.95 | 0.64 |
| | | 100 | 35.25 | 1.76 |
| 500 KD | 40 | 0 | 1.76 | 0.28 |
| | | 100 | 65.12 | 4.82 |
| | 80 | 0 | 2.58 | 0.88 |
| | | 100 | 51.82 | 4.94 |
| 2000 KD | 40 | 0 | 2.24 | 0.18 |
| | | 100 | 105.67 | 9.22 |

What is claimed is:

1. A method for labelling a target substance in or on a solid phase, said method comprising:
providing a labelling composition including:
 (a) a linear polysaccharide having a molecular weight of at least 500 kD;
 (b) a plurality of molecules which specifically bind to the target substance attached to spaced-apart locations along the linear polysaccharide, and
 (c) a multiplicity of fluorescent dye molecules bound to at least some of the target-binding molecules; and
exposing the labelling composition to the solid phase.

2. A method as in claim 1, wherein the solid phase is selected from the group consisting of a polymeric surface, an inorganic surface, and a tissue section.

3. A method as in claim 2, wherein the labelling composition is exposed to a solid phase surface which has previously been prepared by:
providing a solid phase surface having a specific binding substance specific for the target substance immobilized thereon; and
exposing the solid phase to a biological sample suspected of containing the target substance, whereby target substance is bound to the solid phase; and
wherein the labelling composition exposing step comprises exposing the labelling composition to the solid phase.

4. A method as in claim 1, wherein the linear polysaccharide is a dextram.

5. A method as in claim 4, wherein the linear polysaccharide is dextrans having a molecular weight of at least 1000 kD.

6. A method as in claim 1, wherein the target binding molecules are selected from the group consisting of antibodies, antibody fragments, antibody analogs, antigens, nucleic acids, hormones, hormone receptors, enzymes, enzyme substrates, avidin, and streptavidin.

7. A method as in claim 1, wherein the linear polysaccharide is dextrans having a molecular weight of at least 1000 kD and the target binding molecule is an antibody.

8. A method as in claim 1, wherein the fluorescent dye molecules are cyanine dyes.

9. A method as in claim 8, wherein the cyanine dyes are arylsulfonate cyanines.

10. A method as in claim 9, wherein the arylsulfonate cyanine is Cy5.

11. A method as in claim 1, wherein each target-binding molecule has from 1 to 10 fluorescent dye molecules covalently bound thereto.

12. A method as in claim 1, wherein the linear polysaccharide is dextrans having a molecular weight of at least 1000 kD, the target binding molecule is an antibody, and the fluorescent dye is an arylsulfonate cyanine.

* * * * *